United States Patent [19]

Schickaneder et al.

[11] Patent Number: 4,578,389
[45] Date of Patent: Mar. 25, 1986

[54] QUINAZOLINE AND MEDICAMENTS CONTAINING THESE COMPOUNDS

[75] Inventors: Helmut Schickaneder, Eckental; Istvan Szeleny, Schwaig; Peter Mörsdorf, Cadolzburg; Kurt H. Ahrens, Nuremberg, all of Fed. Rep. of Germany

[73] Assignee: Ludwig Heumann & Co. GmbH, Nuremberg, Fed. Rep. of Germany

[21] Appl. No.: 649,099

[22] Filed: Sep. 10, 1984

[30] Foreign Application Priority Data

Oct. 6, 1983 [DE] Fed. Rep. of Germany ..... 33364095

[51] Int. Cl.⁴ ................ A61K 31/505; C07D 403/14
[52] U.S. Cl. ........................... 514/254; 514/218; 544/284; 544/291; 260/243.3
[58] Field of Search ..................... 544/291, 284; 260/243.3; 514/218, 254

[56] References Cited

U.S. PATENT DOCUMENTS 4,351,832  9/1982  Rakhitg et al. ............... 544/284
4,377,581  3/1983  Hess et al. .................... 544/284

FOREIGN PATENT DOCUMENTS

WO/0000166  4/1979  PCT Int'l Appl. ............... 544/284

Primary Examiner—Glennon H. Hollrah
Assistant Examiner—James H. Turnipseed

[57] ABSTRACT

The invention relates to quinazoline derivatives corresponding to the following general formula

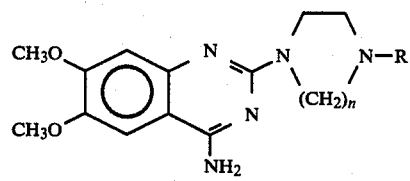

in which R is a mono- to trisubstituted 5-ring heterocycle from the group comprising triazoles, oxadiazoles, thiazoles and imidazoles, the heterocycle being attached to the piperazine or homopiperazine ring by a carbon atom, and n has a value of 2 or 3, or R represents an N-cyanophenyl imidocarbonate group, and to physiologically compatible salts thereof, to processes for their production and to medicaments containing these compounds.

6 Claims, No Drawings

QUINAZOLINE AND MEDICAMENTS CONTAINING THESE COMPOUNDS

DESCRIPTION

This invention relates to new quinazoline derivatives having an antihypertensive effect, to a process for their production and to medicaments containing these compounds and, finally, to the therapeutic use of these compounds.

An active substance from the class of quinazoline derivatives known as "PRAZOSIN" is already therapeutically used as an antihypertensive because it selectively blockades the $\alpha_1$-receptors without blocking $\alpha_2$-receptors.

The object of the present invention is to provide new compounds having improved antihypertensive activity.

This object is achieved by the invention.

Accordingly, the present invention relates to new quinazoline derivatives corresponding to the following general formula

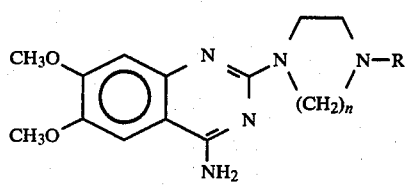

in which:

R is a mono- to trisubstituted 5-ring heterocycle from the group comprising triazoles, oxadiazoles, thiazoles and imidazoles, the heterocycle being attached to the piperazine or homopiperazine ring by a carbon atom, and n has a value of 2 or 3, or R represents an N-cyanophenyl imidocarbonate group, and to physiologically compatible salts thereof. In general formula I, R represents a mono- to trisubstituted 5-ring heterocycle, namely a triazole, oxadiazole, thiazole or imidazole, such as for example 1,2,4-triazole, 1,2,4-oxadiazole, 1,3-thiazole and 1,3-imidazole.

The 5-ring heterocycle mentioned may be substituted 1 to 3 times, the disubstitution being preferred in the case of the triazole ring and the thiazole ring. In the case of the oxadiazole ring and the imidazole ring, the monosubstitution is preferred.

The substituents in question include, for example, the following groups: lower alkyl groups, lower alkoxy groups, carboxyalkyl groups and optionally substituted, particularly lower-alkyl-substituted, amino groups. Lower alkyl groups and unsubstituted amino groups are preferred.

In the context of the invention, "lower alkyl groups", "lower alkoxy groups" etc. are understood to be groups containing from 1 to 4 carbon atoms in the alkyl portion. Examples of groups such as these are methyl groups, ethyl groups and isopropyl groups, methyl and ethyl groups being preferred.

Thus, in general formula I for example, R is a 1,2,4-triazole ring substituted in the 3 position by an amino group which may optionally carry linear or branched-chain lower alkyl radicals. One example of such a group is the dimethylamino group.

In addition, R may be, for example, a 1,2,4-triazole ring substituted in the 1 position by lower alkyl groups, preferably methyl or ethyl groups, and in the 3 or 5 position by an amino group which may optionally carry linear or branched-chain lower alkyl radicals. A 1,2,4-triazole ring disubstituted in the 1 and 3 positions of the aromatic heterocyclic system is preferred.

In addition, R may also represent, for example, a 1,2,5-thiadiazole-1-oxide ring substituted in the 4 position by a lower alkoxy group, preferably a methoxy group or ethoxy group.

Where R is a 1,3-thiazole ring, this heterocycle may be substituted in the 4 position by an amino group and in the 5 position by a carboxyalkyl group, preferably a carboxyethyl group.

Finally, R may also represent the group

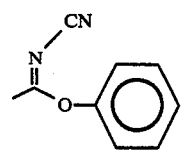

The present invention also relates to the physiologically compatible salts of these new quinazole derivatives.

These salts may be formed, for example, with mineral acids, such as hydrochloric acid, hydrobromic acid and hydriodic acid, phosphoric acid, metaphosphoric acid, nitric acid or sulfuric acid, or with organic acids, such as formic acid, acetic acid, propionic acid, phenyl acetic acid, tartaric acid, citric acid, fumaric acid, methane sulfonic acid, etc.

The present invention also covers all tautomeric forms and salts thereof. The compounds according to the invention may form disalts and trisalts and also hydrates which also fall within the scope of the present invention.

The compounds according to the invention are produced by a process which is characterized in that (a) to produce compounds corresponding to general formula I in which R represents the group

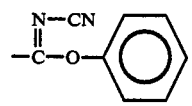

a compound corresponding to the following general formula

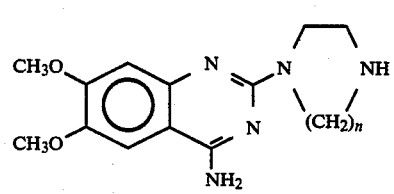

in which n is as defined above, is reacted for 80 minutes at 25° to 82° C., preferably at room temperature, with equimolar quantities of N-cyano diphenyl imidocarbonate corresponding to the following formula

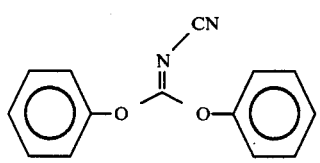

in an alcohol, preferably in isopropanol, to form the compound of general formula Ia according to the invention

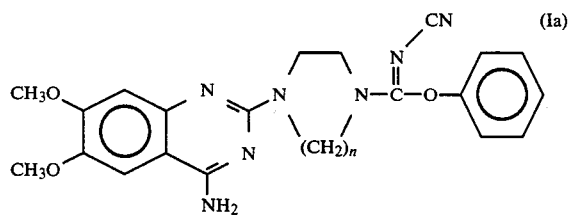

in which n is as defined above, or (b) to produce compounds corresponding to general formula I, in which R is a 1,2,4-triazole or 1,3-thiazole, a compound corresponding to general formula Ia is reacted with a hydrazine derivative or mercaptoacetic acid ester in an alcoholic solvent, preferably methanol, at reflux temperature to form a compound of general formula Ic, Id, Ie or If according to the invention

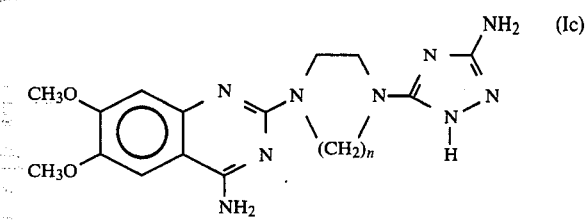

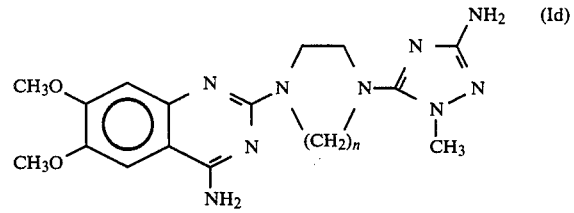

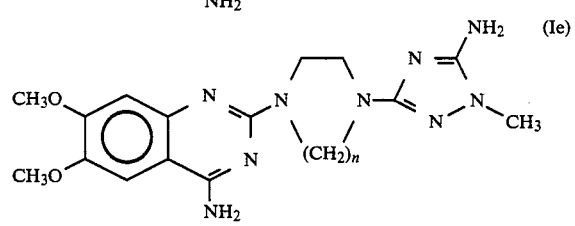

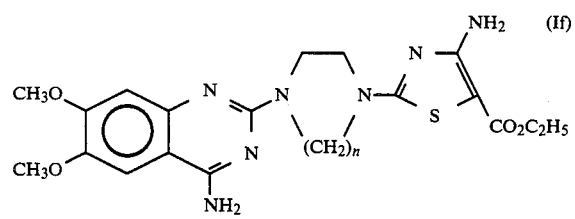

and in that the compound obtained in steps (a) or (b) is optionally converted into a physiologically compatible salt.

The compound of general formula I obtained is isolated in the usual way, for example by crystallization.

The compound of general formula I obtained may be converted into a salt in known manner using a pharmacologically compatible acid.

The compounds according to the invention, preferably in the form of a salt, may be formulated in any way for administration. Accordingly, the invention also relates to medicaments containing at least one compound according to the invention for use in human or veterinary medicine. The medicaments according to the invention may be conventionally produced using one or more pharmaceutically compatible carriers or diluents.

Accordingly, the compounds according to the invention may be formulated for oral, buccal and parenteral administration, oral administration being preferred. For oral administration, the medicament may be present, for example, in the form of tablets, capsules, powders, solutions, syrups or suspensions which have been conventionally produced using acceptable diluents. For buccal administration, the medicament may assume the form of tablets or capsules which have been conventionally formulated.

The compounds according to the invention may be formulated for parenteral administration by bolus injection or continuous infusion. Formulations for injection may be present in unit dose form as ampoules or in multiple-dose containers with added preservative.

The medicaments may assume such forms as suspensions, solutions or emulsions in oily or aqueous carriers and may contain formulation aids, such as suspending agents, stabilizers and/or dispersants. Alternatively, the active principle may even be present in powder form for reconstitution before use with a suitable carrier, for example sterile, pyrogen-free water.

For oral administration, a suitable daily dose of compounds according to the invention is from 1 to 4 doses containing a total of up to ⅓ mg–20 mg per day, depending on the condition of the patient. In individual cases, it may be necessary to vary the dosage in dependence upon the reaction of the individual to the active principle or its formulation and upon the time at which or intervals at which it is administered. For example, there are cases where it will be sufficient to administer less than the minimum dose specified above, whereas in other cases the dose administered will have to exceed the upper limit indicated.

The dosage for intravenous administration amounts to between about 1/5th and 1/10th of the oral daily dose.

Pharmacological Activity

The new compounds according to the invention are distinguished from recognized medicaments acting in the same direction by an improvement in the pharmacological activity levels. This is reflected in the results of the comparative pharmacological tests described in the following.

A recognized method is to determine the blood-pressure-reducing effect in spontaneously hypertensive rats. The rats used had a starting weight of 160–185 g. Blood pressure was measured nonoperatively by means of a BP Recorder (type 8005, W+W electronic AG, Basel).

An average systolic blood pressure value of 125±6 mm Hg (n=10) was recorded in healthy rats (SIV 50, Dr. Ivanovas, Kisslegg, 160 to 180 g). The antihypertensive effect of the above-mentioned compounds was expressed in % taking the normal systolic value into account, a 100% effect signifying a reduction in blood pressure to the normal level of 125 mm Hg.

Prazosin was used for comparison.
$ED_{50}$ (Prazosin): 0.7 mg/kg p.o.
$ED_{50}$ (Example 4): 0.17 mg/kg p.o.

The other Examples show similar pharmacological activities.

The invention is illustrated by the following Examples.

EXAMPLE 1

N-cyano-[(4-amino-6,7-dimethoxyquinazolin-2-yl)-N,N-tetramethylene-4-imino]-phenylisourea

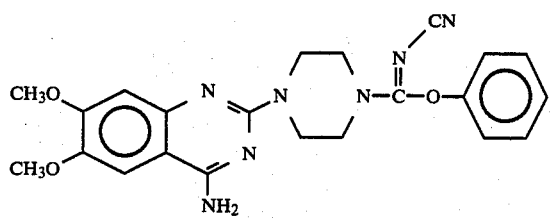

2.89 g (10 mMoles) of 4-amino-6,7-dimethoxy-2-piperazinoquinazoline and 2,38 g (10 mMoles) of N-cyanodiphenylimidocarbonate are suspended in 100 ml of isopropanol and heated for 3 hours to 50° C. The reaction mixture is then allowed to cool and the solids are separated off. Colorless crystals melting at 243° to 244° C.

Yield: 3.77 g (87%)

---

Rf: 0.64 (ethylacetate/ethanol 7:3)
$C_{22}H_{23}N_7O_3$ (433)
$^1$H—NMR—data:  δ = 3.50–4.13 (m)(2 × OC$\underline{H}_3$;

(d$_6$-DMSO, TMS as internal standard)

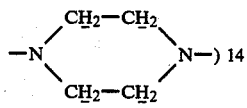

6.77 (s)(aromatic-$\underline{H}$) 1 H,
7.03–7.63 (m)(aromatic-$\underline{H}$, —N$\underline{H}_2$) 8 H ppm.

---

EXAMPLE 2

3-ethoxy-4-[4-(4-amino-6,7-dimethoxyquinazolin-2-yl)-piperazin-1-yl]-1,2,5-thiadiazole-1-oxide

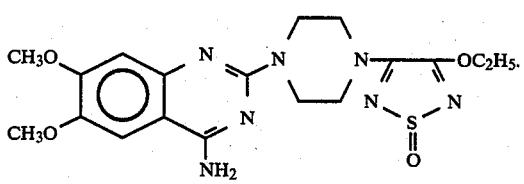

1.9 g (10 mMoles) of 3,4-diethoxy-1,2,5-thiadiazole-1-oxide are added to 2.9 g (10 mMoles) of 4-amino-6,7-dimethoxy-2-piperazinoquinazoline dissolved in 50 ml of tetrahydrofuran and 10 ml of methanol, followed by stirring for 5 hours at room temperature. The solid accumulating is separated off and recrystallized from 15 ml of dimethyl formamide and 10 ml of ethanol.

Yellow crystals melting at 234°–235° C.
Yield: 3.01 g (70% of the theoretical)

---

Rf: 0.57 (ethylacetate/ethanol 70:30)
Cphd $18H_{23}N_7O_4S$ (433)
$^1$H—NMR spectrum:  δ = 1.43 (t) (C$\underline{H}_3$—CH$_2$) 3 H,
(d$_6$-DMSO, TMS as internal standard)
3.60–4.10 (m) (2 × N(C$\underline{H}_2$)$_2$;
(2 × OC$\underline{H}_3$) 14 H,
4.5 (q) (CH$_3$C$\underline{H}_2$) 2 H,
6.77 (s) (aromatic-$\underline{H}$) 1 H,
7.13 (s) (—N$\underline{H}_2$) 2 H (replaceable by D$_2$O)
7.47 (s) (aromatic-$\underline{H}$) 1 H ppm.

---

EXAMPLE 3

4-amino-2-[4-(3-amino-1H-1,2,4-triazol-5-yl)-piperazin-1-yl]-6,7-dimethoxyquinazoline

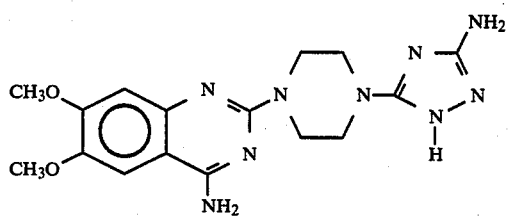

4.33 g (10 mMoles) of N-cyano-[(4-amino-6,7-dimethoxyquinazolin-2-yl)-N,N-tetramethylene-4-imino]-phenylisourea are dissolved with 0.5 g (10 mMoles) of hydrazine hydrate in 20 ml of methanol and the resulting solution heated for 20 minutes to relfux temperature. After cooling to room temperature, the reaction solution is concentrated in vacuo. The residue is recrystallized from methanol.

Colorless crystals melting at 172° to 173° C. (decomp.).

Yield: 2.94 g (79% of the theoretical)

---

Rf: 0.65 (methanol/NH$_3$—conc. 99:1)
$C_{16}H_{21}N_9O_2$ (371)
$^1$H—NMR-spectrum:  δ = 3.27 (m) (—N(C$\underline{H}_2$)$_2$) 4 H,
(d$_6$-DMSO, TMS as internal standard)
3.63–4.00 (m) (N(—C$\underline{H}_2$)$_2$) 4 H,
3.80 (s) (—OC$\underline{H}_3$) 3 H,
3.85 (s) (—OC$\underline{H}_3$) 3 H,
5.63 (s,broad) (N$\underline{H}_2$) 2 H (replaceable by D$_2$O)
6.78 (s) (aromatic-$\underline{H}$) 1 H,
7.12 (s,broad) (N$\underline{H}_2$) 2 H (replaceable by D$_2$O)
7.47 (s) (aromatic-$\underline{H}$) 1 H,
11.57 (s,broad) (N—$\underline{H}$) (replaceable by D$_2$O) ppm.

EXAMPLE 4

4-amino-2-[4-(5-amino-1-methyl-1H-1,2,4-triazol-5-yl)-piperazin-1-yl]-6,7-dimethoxyquinazoline

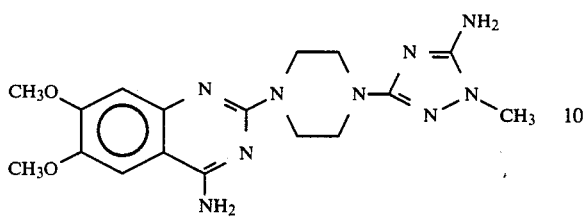

This compound is produced as in Example 3 from 4.33 g (10 mMoles) of N-cyano-[(4-amino-6,7-dimethoxyquinazolin-2-yl)-N,N-tetramethylene-4-imino]-phenylisourea and 0.4 g (10 mMoles) of methyl hydrazine.

Colorless crystals melting at >280° C.

Rf: 0.32 (EtOAc/MeOH 50:50)
$C_{17}H_{23}O_2N_9$ (385).½ $H_2O$     Calc: C 51.78 H 6.59 N 31.98
                                        Found: C 51.80 H 6.18 N 31.54

$^1$H—NMR—spectrum:
(d$_6$-DMSO, TMS as internal standard)

$\delta = 3.23$ (m)(N$\underset{CH_2}{\overset{CH_2}{\diagdown}}$) 4 H, 3.33 (s)(N—C$\underline{H}_3$) 3 H, 3.57–4.03 (m)(N$\underset{CH_2}{\overset{CH_2}{\diagdown}}$) 4 H, 3.80 (s)(OC$\underline{H}_3$) 3 H,
3.83 (s)(OC$\underline{H}_3$) 3 H,
6.00 (s)(—N$\underline{H}_2$) 2 H
(replaceable by D$_2$O)
6.77 (s)(aromatic-$\underline{H}$) 1 H,
7.10 (s, broad)(—N$\underline{H}_2$) 2 H
(replaceable by D$_2$O)
7.47 (s)(aromatic-$\underline{H}$) 1 H, ppm.

EXAMPLE 5

4-amino-2-[4-(3-amino-1-methyl-1H-1,2,4-triazol-5-yl)-piperazin-1-yl]-6,7-dimethoxyquinazoline

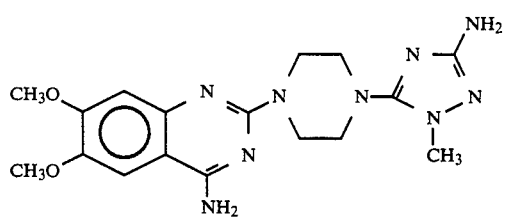

This compound is produced as in Example 3 from 4.33 g (10 mMoles) of N-cyano-[(4-amino-6,7-dimethoxyquinazolin-2-yl)-N,N-tetramethylene-4-imino]-phenylisourea and 0.46 g (10 mMoles) of methyl hydrazine. After the reaction solution has been concentrated, the compound is obtained by fractional crystallization from ethanol/methanol (3:1).

Colorless crystals melting at 250° to 252° C.

Rf: 0.59 (CHCl$_3$/ethanol.NH$_3$[3.3 m]8:2)
$C_{17}H_{23}N_9O_2$ (385)     Calc: C 52.98 H 6.02 N 32.71
                                Found: C 53.07 H 6.00 N 32.61

$^1$H—NMR—spectrum:
(d$_6$-DMSO, TMS as internal standard)

$\delta = 3.13$ (m)(N$\underset{CH_2}{\overset{CH_2}{\diagdown}}$) 4 H, 3.50 (s)(N—C$\underline{H}_3$) 3 H, 3.73–4.03 (m)(N$\underset{CH_2}{\overset{CH_2}{\diagdown}}$) 4 H, 3.77 (s)(OC$\underline{H}_3$) 3 H,
3.81 (s)(OC$\underline{H}_3$) 3 H,
5.00 (s)(—N$\underline{H}_2$) 2 H
(replaceable by D$_2$O)
6.77 (s)(aromatic-$\underline{H}$) 1 H,
7.13 (s, broad)(—N$\underline{H}_2$) 2 H
(replaceable by D$_2$O)
7.47 (s)(aromatic-$\underline{H}$) 1 H ppm.

EXAMPLE 6

4-amino-2-[4-(4-amino-5-carbethoxythiazol-2-yl)-piperazin-1-yl]-6,7-dimethoxyquinazoline

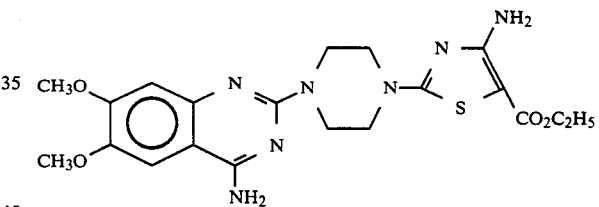

4.33 g (10 mMoles) of N-cyano-[(4-amino-6,7-dimethoxyquinazolin-2-yl)-N,N-tetramethylene-4-imino]-phenylisourea, 1.6 ml (14.8 mMoles) of thioglycolic acid ethyl ester and 20 ml of triethylamine are heated under reflux for 7 hours in 20 ml of methanol. After the reaction solution has cooled to room temperature, the reaction product is filtered off under suction and recrystallized from acetone.

Colorless crystals melting at 189° to 190° C.
Yield: 3.72 g (81% of the theoretical)

Rf: 0.52 (CH$_2$Cl$_2$/CH$_3$OH 90:10)
$C_{20}H_{25}N_7O_4S$ (450)     Calc: C 52.28 H 5.48 N 21.34
                                Found: C 52.38 H 5.47 N 21.32

$^1$H—NMR-spectrum:
(d$_6$-DMSO, TMS as internal standard)

$\delta =$ 1.20 (t) (CH$_3$—C$\underline{H}_2$) 3 H,
3.53 (m, broad) (—N(C$\underline{H}_2$)$_2$) 4 H,
3.67–3.97 (m) (N(—C$\underline{H}_2$)$_2$) 4 H,
3.77 (s) (OC$\underline{H}_3$) 3 H,
3.83 (s) (OC$\underline{H}_3$) 3 H,
4.08 (q) (CH$_3$C$\underline{H}_2$) 2 H,
6.77 (s, broad) (aromatic-$\underline{H}$), N$\underline{H}_2$) 3 H
(replaceable by D$_2$O
7.13 (s, broad) (—N$\underline{H}_2$) 2 H
(replaceable by D$_2$O)
7.47 (s) (aromatic-$\underline{H}$) 1 H ppm.

EXAMPLE 7

4-amino-2-[4-(3-amino-1-methyl-1H-1,2,4-triazol-5-yl)-homopiperazin-1-yl]-6,7-dimethoxyquinazoline

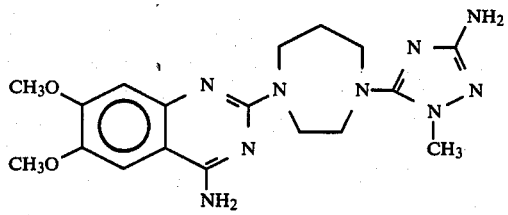

4.47 g (10 mMoles) of N-cyano-[(4-amino-6,7-dimethoxyquinazolin-2-yl)-N,N-pentamethylene-4-imino]-phenylisourea are dissolved with 0.46 g (10 mMoles) of methyl hydrazine in 20 ml of methanol and the resulting solution heated for 5 hours to reflux temperature. After cooling to room temperature, the reaction solution is concentrated in vacuo. The residue is purified by column chromatography on silica gel (eluent:CHCl$_3$/triethylamine in EtOH 3.3 molar).

Light yellow crystals melting at 128° to 132° C.

---

Rf: 0.58 (CHCl$_3$/triethylamine in EtOH [3.3 m]70:30)

C$_{18}$H$_{25}$N$_9$O$_2$ (399)

$^1$H—NMR—spectrum:  δ = 1.92 (m)(—C$\underline{H}_2$) 2 H, (d$_6$-DMSO, TMS as internal standard)

3.13–3.50 (m)(N$\diagup^{CH_2}_{\diagdown CH_2}$) 4 H, 3.38 (s)(—C$\underline{H}_3$) 3 H, 3.63–4.23 (m)(N$\diagup^{CH_2}_{\diagdown CH_2}$) 4 H, 3.77 (s)(—OC$\underline{H}_3$) 3 H, 3.83 (s)(—OC$\underline{H}_3$) 3 H, 4.87 (s)(—N$\underline{H}_2$) 2 H (replaceable by D$_2$O)

6.73 (s)(aromatic-$\underline{H}$) 1 H, 7.03 (s)(N$\underline{H}_2$) 2 H (replaceable by D$_2$O)

7.43 (s)(aromatic-$\underline{H}$) 1 H ppm.

EXAMPLE 8

4-amino-2-[4-(5-amino-1-methyl-1H-1,2,4-triazol-3-yl)-homopiperazin-1-yl]-6,7-dimethoxyquinazoline

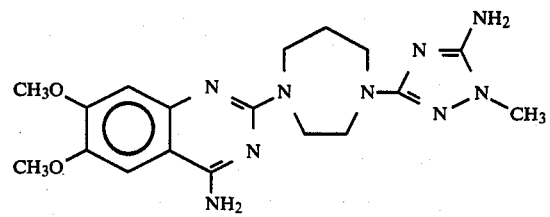

This compound is produced as in Example 7. The end product is purified by column chromatography as described in Example 7.

Light yellow crystals melting at 208° C. (decomp.).

---

Rf: 0.37 (CHCl$_3$/triethylamine in EtOH [3.3 m]70:30)

C$_{18}$H$_{25}$N$_9$O$_2$ (399)

$^1$H—NMR—spectrum:  δ = 1.90 (m)(—C$\underline{H}_2$) 2 H, (d$_6$-DMSO, TMS as internal standard)

3.17–3.93 (2 × N$\diagup^{CH_2}_{\diagdown CH_2}$) 8 H, 3.30 (s)(—C$\underline{H}_3$) 3 H,
3.80 (s)(—OC$\underline{H}_3$) 3 H,
5.83 (s)(N$\underline{H}_2$) 2 H
(replaceable by D$_2$O)
6.67 (s)(aromatic-$\underline{H}$) 1 H,
7.04 (s)(N$\underline{H}_2$) 2 H
(replaceable by D$_2$O)
7.33 (s)(aromatic-$\underline{H}$) 1 H ppm

We claim:
1. Quinazoline derivatives corresponding to the following formula

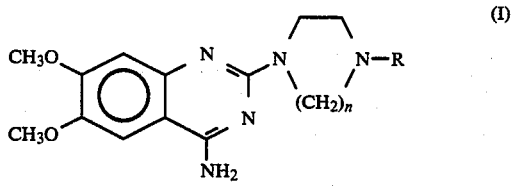

(I)

in which:
R represents a triazole ring which is substituted in the 1-position by a methyl group and in the 3-position or the 5-position by an amino group, the triazole ring being attached to the piperazine or homopiperazine ring through a carbon atom, and n has a value of 2 or 3, and physiologically compatible salts thereof.

2. 4-amino-2-[4-(3-amino-1-methyl-1H-1,2,4-triazol-5-yl)-piperazin-1-yl]-6,7-dimethoxyquinazoline and physiologically compatible salts thereof.

3. 4-amino-2-[4-(5-amino-1-methyl-1H-1,2,4-triazol-3-yl)-piperazin-1-yl]-6,7-dimethoxyquinazoline and physiologically compatible salts thereof.

4. A medicament containing an antihypertensive effective amount of a compound as claimed in claim 1 together with an inert pharmaceutically compatible carrier or an inert pharmaceutically compatible diluent.

5. A medicament containing an antihypertensive effective amount of a compound as claimed in claim 2 together with an inert pharmaceutically compatible carrier or an inert pharmaceutically compatible diluent.

6. A medicament containing an antihypertensive effective amount of a compound as claimed in claim 3 together with an inert pharmaceutically compatible carrier or an inert pharmaceutically compatible diluent.

* * * * *